United States Patent [19]
Paakkinen

[11] Patent Number: 4,959,994
[45] Date of Patent: Oct. 2, 1990

[54] METHOD OF AND AN ARRANGEMENT FOR MEASURING THE PROPERTIES OF A STIFF MASS TO BE COMPACTED

[76] Inventor: Ilmari Paakkinen, PPA 1, Moinsalmi, SF-57230 Savonlinna, Finland

[21] Appl. No.: 417,901

[22] Filed: Oct. 6, 1989

[30] Foreign Application Priority Data

Oct. 11, 1988 [FI] Finland .................................. 884666

[51] Int. Cl.$^5$ ...................... G01N 15/08; G01N 33/38
[52] U.S. Cl. .......................................................... 73/38
[58] Field of Search ............................ 73/38, 37, 64.1

[56] References Cited

U.S. PATENT DOCUMENTS 3,335,787 8/1967 Dietert et al. ...................... 73/38 X

FOREIGN PATENT DOCUMENTS

| 3628955 | 3/1988 | Fed. Rep. of Germany | 73/38 |
| 50643 | 3/1982 | Japan | 73/38 |
| 684403 | 9/1979 | U.S.S.R. | 73/38 |
| 690369 | 10/1979 | U.S.S.R. | 73/38 |
| 759958 | 9/1980 | U.S.S.R. | 73/38 |

Primary Examiner—John Chapman
Assistant Examiner—Joseph W. Roskos
Attorney, Agent, or Firm—Fitch, Even, Tabin & Flannery

[57] ABSTRACT

The invention relates to a method and an arrangement for measuring the properties, particularly the degree of compaction of a stiff compactable mass such as fresh concrete, to be cast or a similar soil mass. In order to make the control of compaction more effective, gaseous pressure fluid is blown through the mass during the compaction of the mass, simultaneously, observing increases in the pressure of the gaseous pressure fluid in the surface portions of the mass due to increased flow resistance. The pressure fluid is blown through an opening formed in a wall adjoining the mass to be compacted and by means of a source of pressure fluid connected to the opening. Changes in the flow resistance are measured by means of a measuring device.

19 Claims, 1 Drawing Sheet

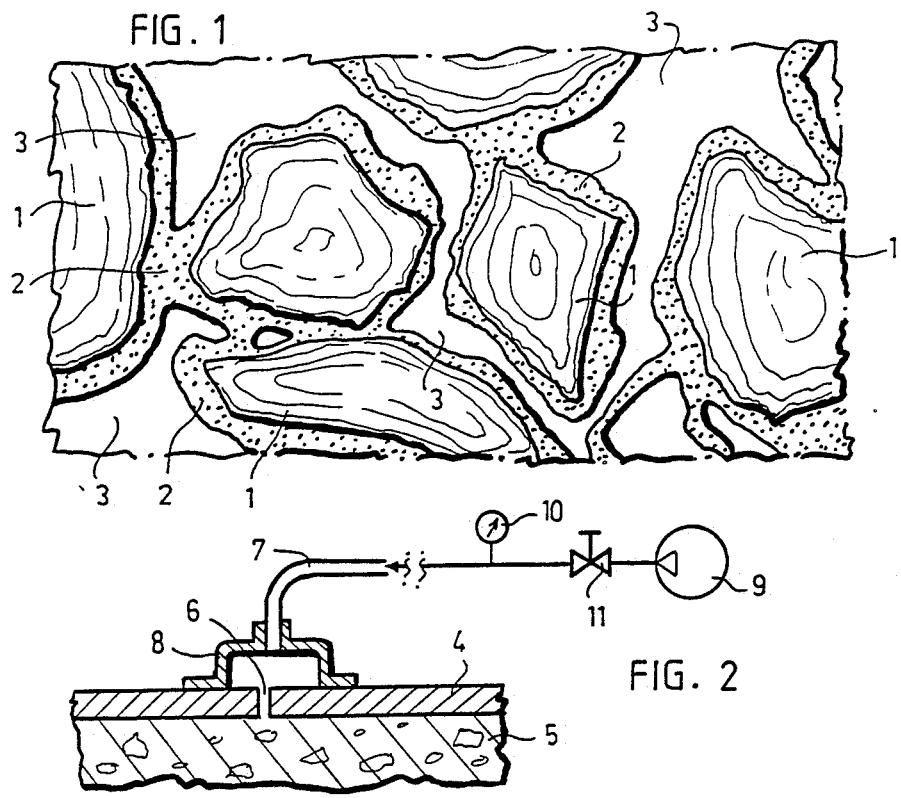
FIG. 1
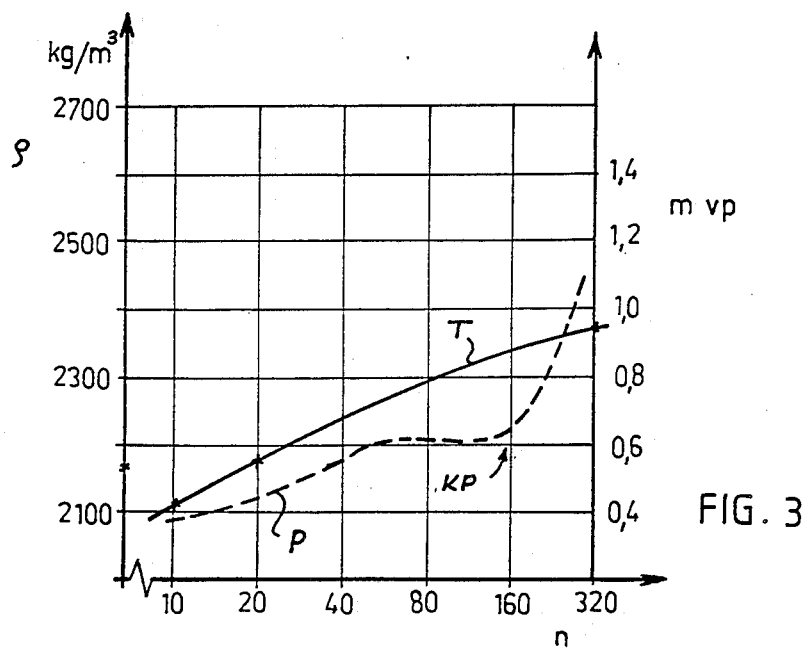
FIG. 2
FIG. 3

METHOD OF AND AN ARRANGEMENT FOR MEASURING THE PROPERTIES OF A STIFF MASS TO BE COMPACTED

BACKGROUND OF THE INVENTION

The invention relates to a method of and an arrangement for measuring the properties, particularly the degree of compaction of a stiff mass to be compacted, such as fresh concrete to be cast and similar soil mass.

The use of concrete masses containing ever decreasing amounts of water has been on the increase in concrete industries. This is due to the fact that, generally speaking, the strength values provided by the mass are better, the lower the water content of the mass, provided that the mass can be compacted effectively. In practice, an amount of water of 20-30% of the amount of cement is sufficient for hydration, that is, the W/C ratio ranges from 0.20 to 0.30. Furthermore, cement is today ground very fine in order that the concrete strength to be obtained by it could be utilized better and more rapidly. Such masses, called soil moist masses, are difficult to mould and cast. Such masses are often called stiff masses.

Stiff masses are used, e.g., in modern slip casting processes, and in roll compaction. Even though there are various useful methods and apparatuses for measuring the properties of plastic masses, such as the degree of compaction, there are no suitable methods and apparatuses for accurately measuring the degree of compaction of stiff masses. The greater the degree of compaction of concrete in the finished cast product, the greater the strength obtained. Therefore, information on the compacting properties of a concrete mass to be cast is very important to obtain a good end result.

The compactability of concrete is substantially dependent on the "stiffness" of the mass, that is, in general, its water content. When the mass is too stiff, the cast has poor compacting properties and many air pores remain within the cast. When the mass is too plastic, it apparently contains excess water, which deteriorates the strength. The end result is inferior, and the shape and tolerances of the cast are difficult to control when casting without a fixed mould. The compactability of concrete is not only affected by the amounts of ingredients and the mix proportions, but also by the quality and size of the ingredients and other factors. For this reason reliable information on the compacting properties of the mass is of vital importance.

In the absence of suitable measuring methods and apparatuses, evaluation by feeling with the hands has been used previously in an attempt to measure the compacting properties of stiff concretes. Such evaluation, however, requires high professional skill and is nevertheless always unreliable and subjective and consequently, cast products are often rejected.

An example of more advanced measuring methods and apparatuses for stiff masses is disclosed in FI Patent Specification 71619. This method is an indirect method in which a sample is taken from the mass to observe the process. Increase in the density of the sample indicates an increased degree of compaction. The method is applicable only in cases where the properties are measured by sampling. Information provided by the method of FI Patent Specification 71619 is not sufficient for research work, for example, but information on other compacting properties is required. For example, variation in the quality of stone aggregate must be accurately determined and taken into account. The specific weight of the stone aggregate must be accurately determined as it affects the density measurements.

In addition to fresh concrete to be cast, there are other masses which are measured for their properties, such as soil and bitumen masses.

The object of the invention is to provide a method and an arrangement by means of which the drawbacks of the prior art can be eliminated, and which enables the degree of compaction of a stiff mass to be measured more accurately than was done previously. This is achieved by means of a method and arrangement according to the invention. The method is characterized in that gaseous pressure fluid is blown through the mass during the compaction of the mass, simultaneously observing increases in the pressure of the gaseous pressure fluid in the surface portions of the mass due to increasing flow resistance. The arrangement, in turn, is characterized in that it comprises; an opening formed in a wall adjoining the mass to be compacted, a source of pressure fluid connected to said opening so as to blow gaseous pressure fluid through the opening on to the surface of the mass and further therethrough, and a measuring device for measuring the pressure of the pressure fluid in the surface portions of the mass.

The invention is based on a certain property of a stiff mass to be compacted, that is, on the fact that stiff uncompacted concrete, for instance, contains about 20-50% by volume of air. To illustrate this, assume that concrete contains only large aggregate particles and moist cement paste. In a concrete mixer, the cement has spread everywhere on the surface of the aggregate particles. In uncompacted concrete, there are plenty of air cavities between the aggregate particles covered by cement paste. There are air cavities between the aggregate particles and the cement paste as well. These air cavities form a continuous three-axis network which extends throughout the concrete and in which air, for instance, can easily pass through the concrete. The invention is based on the fact that this network of cavities changes while the concrete is compacted, whereby the flow resistance of air passed through the concrete also changes in a determined manner.

An advantage of the invention is that it enables an efficient control of the compaction of mass, whereby the final product is of desired quality. This reduces the number of rejected products and the waste labour associated therewith. A further advantage of the invention is its wide range of applications: it can be applied both directly at the manufacturing stage, e.g., by utilizing a concrete mould, and with indirect methods known from the prior art. Still another advantage is that the whole mixing formula and the specific weights of the ingredients need not be taken into account in the measuring.

In the following, the invention will be described in greater detail with reference to the attached drawings illustrating an embodiment in which the invention is applied to a concrete mass, whereby:

BRIEF DESCRIPTION OF THE DRAWINGS

FIG. 1 is general sectional view through uncompacted concrete;

FIG. 2 is a general view of an arrangement according to the invention; and

FIG. 3 illustrates an example of a concrete compaction measurement carried out by means of the arrangement of FIG. 2.

DETAILED DESCRIPTION OF THE PREFERRED EMBODIMENT

To facilitate the understanding of the invention, the behaviour of concrete during compaction will be described below. FIG. 1 shows a general sectional view through uncompacted concrete. The representation of FIG. 1 is simplified, it being assumed that concrete consists of large aggregate particles 1 and cement paste 2. Air cavities formed within the concrete are indicated with the reference numeral 3. The air cavities 3 form a network extending throughout the concrete, as mentioned above.

When the uncompacted concrete shown in FIG. 1 is exposed to initial compaction, the aggregate particles 1 move towards each other so that new points of contact are formed therebetween. The cement paste 2 fills up more accurately the interspaces between the aggregate particles, and the network formed by the cavities 3 starts to clog at some points. When the compaction is continued, a point of saturation is obtained at a certain stage. The saturation point occurs in all well-compacted stiff concrete masses when all the air conduits formed by the cavities 3 clog up. Thereby, air entrapped in the cavities within the concrete forms bubbles. The bubbles contain about 1/10 of the air contained in uncompacted concrete.

In final compaction, the air bubbles are forced out of the concrete. The air bubbles thereby entrain wet sludge-like cement paste to the surface of the concrete.

This compaction process can be further illustrated by assuming that the concrete is a structure formed by large aggregate particles 1, cement paste 2 and air cavities 3. During compaction, air is removed until the cement paste fills up substantially all of the interspace. Then the paste begins to extrude from the outer surfaces of the concrete. This begins to happen at the point of saturation, whereby the nature of the compaction process changes to some extent, which is to be seen both in empirical measuring results and in graphic and analytic representations. During initial compaction, the compaction is mainly dependent on the removal of air by the displacement of the aggregate particles relative to each other. After the point of saturation has been reached, the compaction depends mainly on the movement of the liquid cement sludge and air bubbles between the aggregate particles.

In practice, the compaction of concrete often remains so incomplete that not even the point of saturation is achieved. The finished concrete product may nevertheless be of high quality. Strength measurement, however, shows that inadequately compacted concrete is inferior to well-compacted concrete.

In practice, the structure of concrete is considerably more complex, and the compaction described above takes place between both large and small particles. The saturation point, however, is distinctive; after it, air bubbles get increasingly smaller and more round while the compaction goes on. The amount of air entrapped within the concrete is decreased as much as below 1/10 of the original value.

The invention utilizes the change taking place in the network formed by the cavities 3 during the compaction. According to the invention, gaseous pressure fluid is blown through the concrete during compaction, and simultaneously therewith is an observed pressure increase in the gaseous pressure fluid in the surface portions of the concrete due to increasing flow resistance.

The blowing is continued until the pressure has reached a predetermined level. The technique is based on the fact that the pressure fluid is able to flow in the network formed by the cavities 3 through the concrete as long as the network is open. As the compaction continues, the network gradually clogs up, which can be observed as increased flow resistance in the surface portions of the concrete. This is easy to measure as increased fluid pressure.

The present method can be applied, e.g., by means of the arrangement of FIG. 2. In the figure, the reference numeral 4 indicates a wall adjoining concrete 5 to the compacted concrete. The reference numeral 6 indicates an opening formed in the wall 4. A source 9 of compressed air is connected to the opening 6 by means of a pipe connection 7, and a connecting device 8 so as to blow pressure fluid through the opening 6 on to the surface of the concrete 5 and further therethrough as described above. The reference numeral 10 indicates a measuring device for measuring the pressure of the pressure fluid on the surface of the concrete. The reference numeral 11 indicates a valve by which the source 9 of pressure fluid can be closed.

The wall 4 may be e.g. the wall of the production mould of the product, whereby the compaction is observed directly in the product to be prepared. The wall 4 may also be the wall of a mass sample container, whereby the method is utilized in indirect measuring. The pressure fluid source may be, e.g., a compressor. Carbon dioxide, for example, can be used as pressure fluid.

In principle, the arrangement of FIG. 2 operates in the following way. Pressure fluid is applied by means of the compressor through the opening 6 on to the surface of the concrete 5 and further therethrough because, as mentioned above, uncompacted concrete is permeable to gas. The compaction causes the network formed by the cavities 3 within the concrete to clog gradually, whereby the flow resistance of the pressure fluid through the concrete increases. Such an increase in the flow resistance is to be seen as pressure increase in the measuring device 10. When the compaction is continued, the network formed by the cavities 3 clogs up at a certain moment, that is, when the saturation point is reached. Thereby the pressure fluid is no more able to go through the concrete, which is to be seen in the measuring device 10 as an abrupt pressure increase. Information on the moment when the saturation point is achieved is a reliable criterion for the quality control of concrete.

FIG. 3 shows a practical example of the operation described above. In FIG. 3, the vertical axis represents the density of concrete and the horizontal axis represents the advancing of compaction. Density change is shown with the curve T. The righthand vertical side of FIG. 3 is provided with a pressure scale and the curve P illustrates change in the air flow resistance, obtained from the measuring device 10. The saturation point can be seen clearly at point KP, where the flow resistance (pressure) increases abruptly.

The above embodiment is by no means intended to restrict the invention, but the invention can be modified within the scope of the claims in various ways. Accordingly, it is to be understood that the solution of FIG. 2, for instance, is not the only one possible, but solutions of other kind are possible as well. The embodiment of FIG. 2 is to be seen as an example illustrative of the principle of the invention and it should not be regarded as a detailed realization. The opening 6 can be of any shape, such as an elongated slit, and there can be provided as many such openings as may be required. The measuring device 10 can be any pressure measuring device known in the prior art. Even though the invention has been described above by means of the example concerned with concrete, it is obvious that the invention can be applied to the measuring of the properties of other similar masses, as mentioned above. The pressure fluid need not necessarily be air. Other suitable pressure fluids include carbon dioxide.

I claim:

1. A method of measuring the properties, particularly the degree of compaction of a stiff mass to be compacted, such as fresh concrete to be cast and similar soil mass, said method comprising blowing gaseous pressure fluid through the mass during the compaction of the mass, simultaneously observing increase in the pressure of the gaseous pressure fluid in the surface portions of the mass due to increasing flow resistance.

2. A method according to claim 1, wherein the blowing of the gaseous pressure fluid is continued during the compaction of the mass until the pressure has achieved a predetermined level.

3. A method according to claim 1 or 2, wherein the pressure fluid is blown on to the surface of the mass to be compacted through an opening provided in a wall of the production mould of the product or that of a compacting means.

4. The method of claim 3 wherein the gaseous pressure fluid is carbon dioxide.

5. The method of claim 3 wherein the pressure fluid is provided by the step of compressing a gaseous fluid with a compressor.

6. A method according to claim 1 or 2, wherein the pressure fluid is blown on to the surface of a mass sample to be compacted through an opening made in a wall of a mass sample container.

7. The method of claim 6 wherein the gaseous pressure fluid is carbon dioxide.

8. The method of claim 6 wherein the pressure fluid is provided by the step of compressing a gaseous fluid with a compressor.

9. The method of claim 2 wherein the gaseous pressure fluid is carbon dioxide.

10. The method of claim 2 wherein the pressure fluid is provided by the step of compressing a gaseous fluid with a compressor.

11. The method of claim 1 wherein the gaseous pressure fluid is carbon dioxide.

12. The method of claim 11 wherein the pressure fluid is provided by the step of compressing a gaseous fluid with a compressor.

13. The method of claim 1 wherein the pressure fluid is provided by the step of compressing a gaseous fluid with a compressor.

14. An arrangement for measuring the properties, particularly the degree of compaction of a stiff mass to be compacted, such as fresh concrete to be cast or similar soil mass, said arrangement comprising an opening formed in a wall adjoining the mass to be compacted; a source of pressure fluid connected to said opening so as to blow gaseous pressure fluid through the opening on to the surface of the mass and further therethrough; and a measuring device for measuring the pressure of the pressure fluid in the surface portions of the mass.

15. An arrangement according to claim 14, wherein the opening is formed in a wall of the production mould of the product or that of a compacting means.

16. The arrangement of claim 15 wherein the source of pressure fluid is a compressor.

17. An arrangement according to claim 14, wherein the opening is formed in a wall of a mass sample container.

18. The arrangement of claim 17 wherein the source of pressure fluid is a compressor.

19. The arrangement of claim 14 wherein the source of pressure fluid is a compressor.

* * * * *

UNITED STATES PATENT AND TRADEMARK OFFICE
CERTIFICATE OF CORRECTION

PATENT NO. : 4,959,994
DATED : October 2, 1990
INVENTOR(S) : Ilmari Paakkinen It is certified that error appears in the above-identified patent and that said Letters Patent is hereby corrected as shown below:

Column 1, line 55, after "subjective" insert a comma.

Column 2, line 2, after "must" insert --also--.

line 45, after "compaction of" insert --a--.

line 56, insert the title --BRIEF DESCRIPTION OF THE DRAWINGS--.

line 60, delete the title "BRIEF DESCRIPTION OF THE DRAWINGS".

Column 3, line 66, after "therewith" insert a comma.

Signed and Sealed this

Third Day of March, 1992

*Attest:*

HARRY F. MANBECK, JR.

*Attesting Officer*     *Commissioner of Patents and Trademarks*